United States Patent [19]
Burrows et al.

[11] Patent Number: 6,063,123
[45] Date of Patent: May 16, 2000

[54] ACETABULAR INSERT EXTRACTOR AND METHOD FOR USE

[75] Inventors: James William Burrows, Cedar Park; Kenneth Robert Konya, Austin, both of Tex.

[73] Assignee: Sulzer Orthopedics Inc., Austin, Tex.

[21] Appl. No.: 09/121,132

[22] Filed: Jul. 22, 1998

[51] Int. Cl.[7] .................................................. A61F 2/34
[52] U.S. Cl. ................................................. 623/22; 606/86
[58] Field of Search .......................... 623/18, 22; 606/99, 606/86

[56] References Cited

U.S. PATENT DOCUMENTS

| | | | |
|---|---|---|---|
| 5,474,560 | 12/1995 | Rohr, Jr. | 606/99 X |
| 5,725,591 | 3/1998 | DeCarlo, Jr. et al. | 606/99 X |
| 5,830,215 | 11/1998 | Incavo et al. | 606/99 X |
| 5,904,688 | 5/1999 | Gilbert et al. | 606/99 X |
| 5,938,701 | 8/1999 | Hiernard et al. | 606/99 X |

*Primary Examiner*—Jeffrey A. Smith
*Attorney, Agent, or Firm*—Philip S. Lyren; Kenneth S. Barrow

[57] ABSTRACT

A plastic insert is extracted from a metal acetabular shell by an extractor device which includes a seat positioned on the insert. A first guide member is attached to the seat. A second guide member is mounted for lateral movement with the first guide member. An extractor is mounted on the second guide member. The second guide member is movable relative to the first guide member for positioning the extractor adjacent the shell. A fastener is inserted through the first guide member and into the insert for securing the first guide member to the insert. The extractor is advanced into engagement with the shell so that the fastener withdraws the insert from the shell.

23 Claims, 3 Drawing Sheets

ACETABULAR INSERT EXTRACTOR AND METHOD FOR USE

BACKGROUND

The disclosures herein relate generally to hip joint implants and more particularly to an extractor for removing an acetabular insert from a metal shell in a hip joint.

An acetabular shell and insert are mounted in the acetabulum for receiving a hip stem which is implanted in a femur. The hip stem terminates in a metal ball which rotatably fits into a socket in the acetabular insert. Originally, both the hip stem ball and the socket in the acetabular insert were each formed of metal. However, many problems arose from the original metal-to-metal contact due to the materials used, such that mechanical seizing, noise and other unacceptable conflicts occurred.

As a result, a plastic acetabular insert was developed which included a convex surface cemented directly into a reamed socket formed into the acetabulum or inserted into a metal shell. This solution avoided the troublesome metal-to-metal contact of the original metal ball seated in the metal socket, and provided a plastic socket formed in the insert for receiving the metal ball of the hip stem.

An improvement provided a titanium metal shell secured in the socket formed in the acetabulum. A threaded fastener or fasteners could be used to secure the shell to the acetabulum. A plastic modular insert is snapped into the metal shell. The insert includes a plastic socket formed therein for receiving the metal ball of the hip stem.

When it is necessary to remove the plastic insert from the metal shell due to wear of the socket, so that the plastic insert can be replaced, the insert could be pried loose or a screw could be threaded into the plastic insert. The screw threads through the plastic insert and bottoms out against the metal shell. Unable to penetrate the titanium metal shell, the plastic insert rides up on the screw threads and eventually snaps out of the metal shell. This extraction method has the benefit of withdrawing the plastic insert directly outwardly from the metal shell. This is beneficial because the metal shell in some cases, includes a porous convex surface to which the bone of the acetabulum attaches over time. Therefore, any prying or twisting forces applied to eject the plastic insert from the metal shell may actually have a detrimental effect on the attachment between the bone socket and the metal shell.

A problem with the metal ball in the plastic socket is that particles of the plastic (polyethylene) material flake off from wear contact with the metal ball. As these flakes collect, the body reacts to the flakes as foreign matter and as a result, adjacent bone material may eventually resorb or deteriorate away due to the presence of these plastic flakes.

In order to avoid this problem caused by the metal-to-plastic wear, a metal inlay has been inserted into the socket formed in the plastic insert. The metal used for the inlay is a cobalt chrome, which is the same metal as the ball of the hip stem. Thus, progress has come full circle, and once again a metal-to-metal contact exists between the hip stem ball and the insert socket. However, the improved materials and manufacturing methods avoid many of the problems associated with early metal-to-metal wear surfaces in such orthopedic implants.

Although wear is greatly reduced with the latest metal-to-metal ball and socket implants, a problem arises when it is necessary to replace the inlay-insert combination from the metal shell. Due to the presence of the metal inlay in the ball socket of the plastic insert, it is no longer possible to extract the insert from the metal shell by the above-mentioned screw extractor method. This is because the screw will not penetrate the cobalt chrome inlay and therefore, the screw is not accessible to thread through and eject the plastic insert straight out of the shell. As stated above, prying and twisting of the plastic insert is undesirable because of the possibility of damaging the connection between the bone and the abutting convex surface of the metal shell.

Therefore, what is needed is a method and apparatus for extracting the plastic insert from the metal shell without damaging the connection between the metal shell and the abutting bone socket.

SUMMARY

One embodiment, accordingly, provides a method and apparatus for withdrawing the plastic insert directly out of the metal shell without disturbing the connection between the metal shell and the abutting bone socket or damaging the shell. To this end, an acetabular insert extractor is provided and includes a seat having a first guide attached to the seat for receiving a fastener. A second guide is movably connected to the first guide. An extractor arm is movably connected to the second guide.

A principal advantage of this embodiment is that the problems associated with plastic wear and the resultant flaking of plastic material are avoided by the presence of the metal inlay which lines the socket of the plastic insert. The withdrawal of the plastic insert which is not possible by the use of the screw technique is accomplished by the extractor which is movably mounted for advancement relative to the second guide, thus urging the insert directly out of the metal shell without the need to apply a prying or twisting motion to the insert or the metal shell. As a result, the shell and bone connection is not subjected to detrimental forces which could damage their interconnection. Also, the insert can be removed without causing damage to the shell.

DETAILED DESCRIPTION OF THE PREFERRED EMBODIMENT

Figure 1:
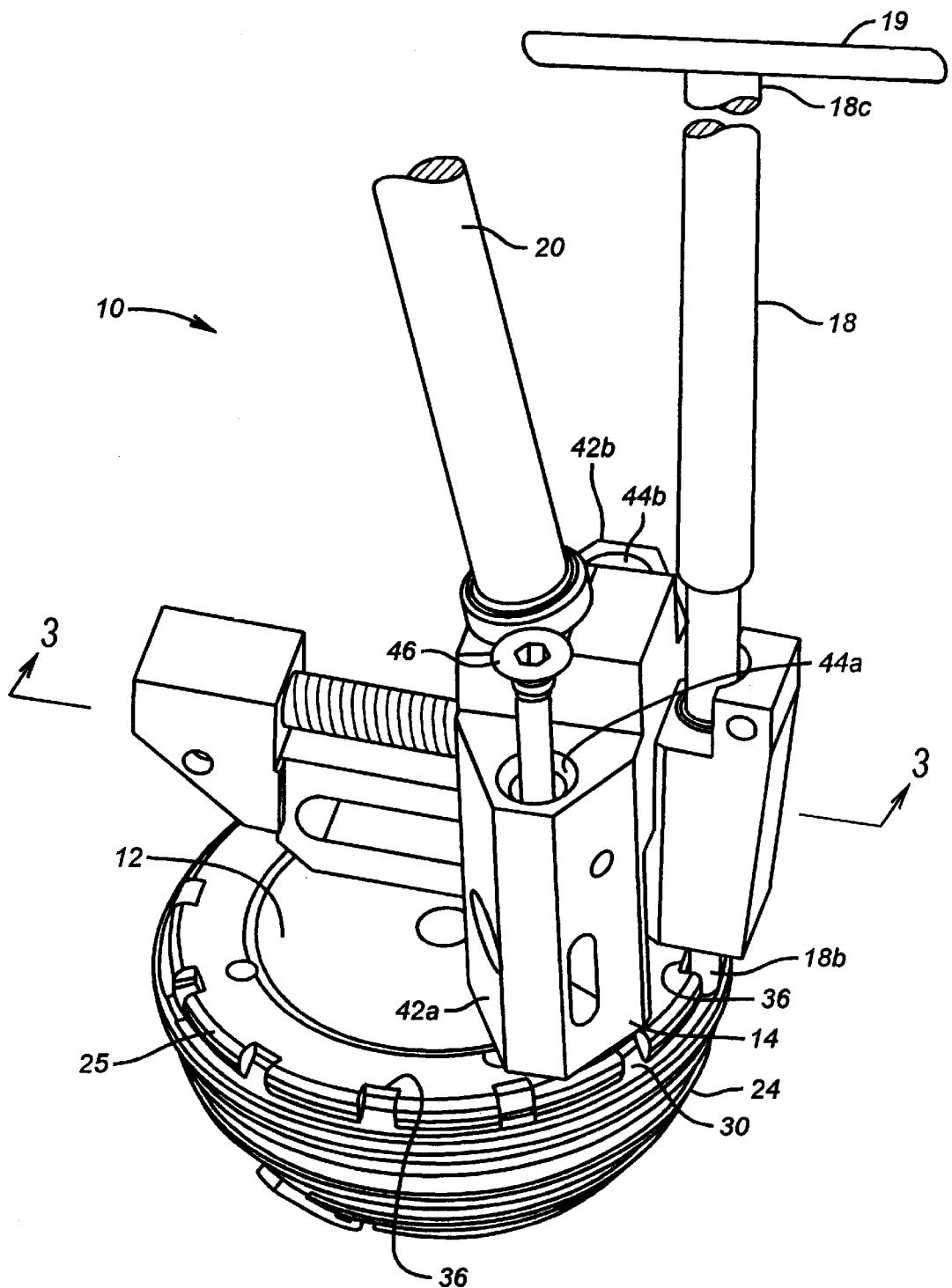
FIG. 1 is an isometric view illustrating an embodiment of the extractor.

An acetabular insert extractor is generally designated 10 in FIG. 1, and includes a seat 12 and a first guide 14 fixedly attached to seat 12. A second guide 16 is movably connected to first guide 14. An extractor arm 18 is movably connected to the second guide 16. Arm 18 may include a handle 19. Also, a stabilizing member 20 is threadably attached to first guide 14.

Figure 2:
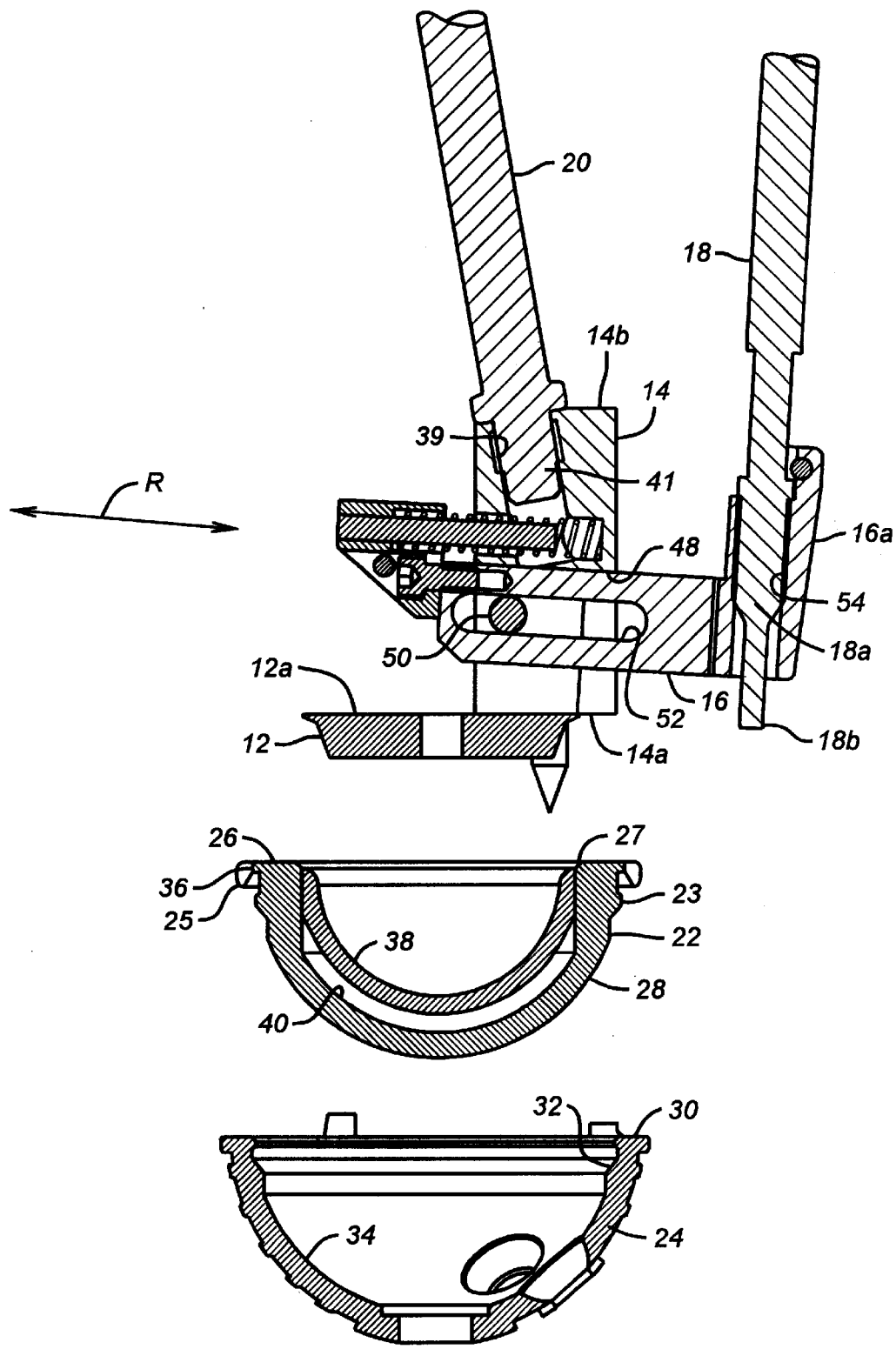
FIG. 2 is a cross-sectional exploded view illustrating an embodiment of the extractor.
Figure 3:
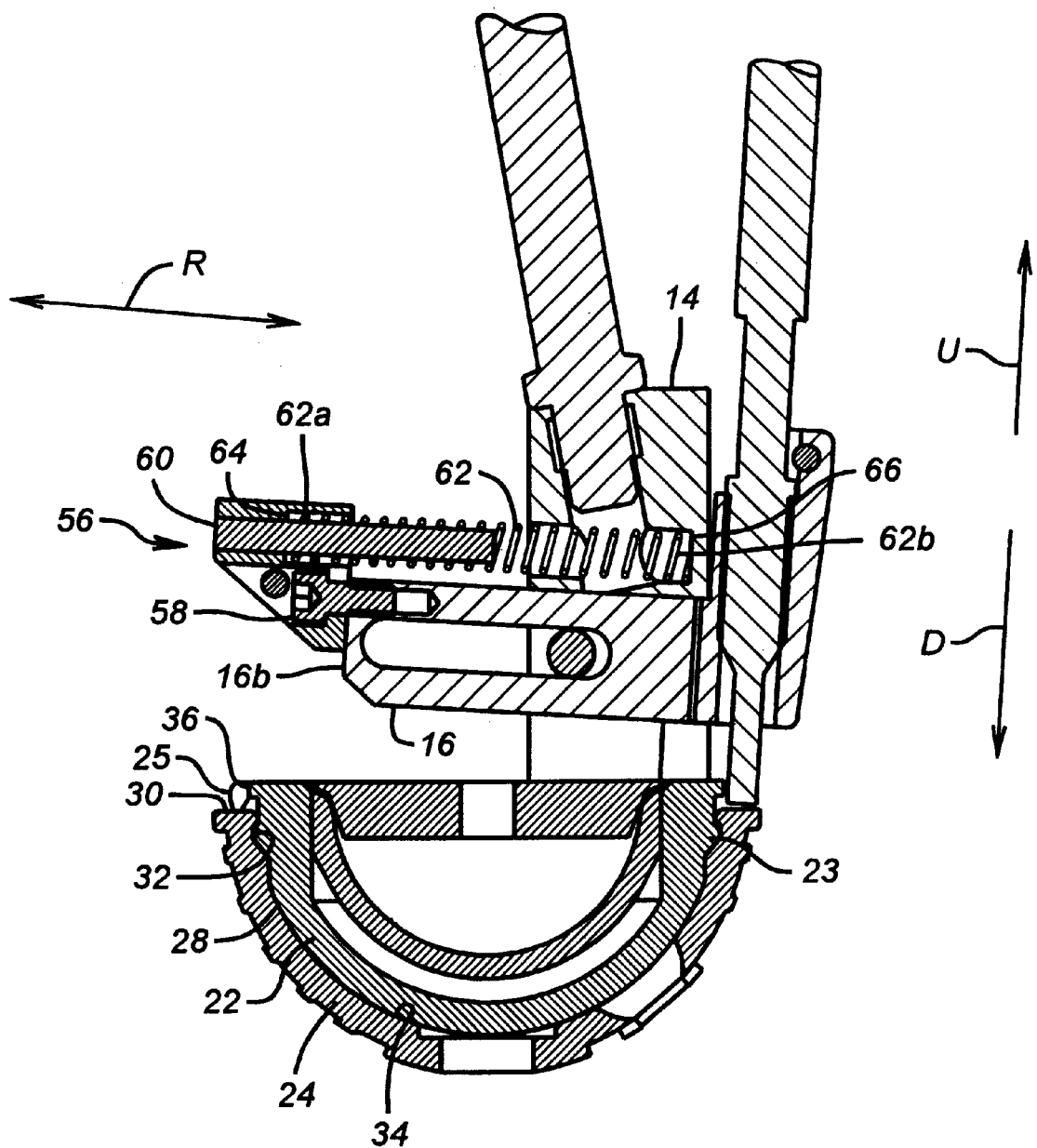
FIG. 3 is a cross-sectional side view illustrating an embodiment of the extractor as viewed from the line 3—3 of FIG. 1.

An acetabular insert 22, FIG. 2, is seated in a shell 24. Insert 22 is formed of a synthetic material such as polyethylene and includes a generally semi-spherical shape having a substantially circular seat 26 surrounding an opening 27. Insert 22 also includes an annular ring 23 formed on an outer surface 28 thereof. Shell 24 is formed of a metal such as titanium and includes a generally semi-spherical shape having a substantially circular seat 30. Shell 24 also includes an annular groove 32 formed in an inner surface 34 thereof. The insert 22 also includes a plurality of radially directed, circumferentially spaced notches 36, FIGS. 1 and 2, formed in a lip 25 of seat 26. Also, a semi-spherically shaped ball socket formed by a cobalt-chrome cup 38, FIG. 2, is fixedly mounted adjacent an inner surface 40 of insert 22. Insert 22, FIG. 3, is securely mounted in shell 24 by being forcibly urged to snap-fit into shell 24 so that annular ring 23 snaps into an interference fit within annular groove 32. In this manner, outer surface 28 of insert 22 is in nested engagement with inner surface 34 of shell 24. Also, lip 25 of insert 22 overhangs circular seat 30 of shell 24 such that notches 36 of insert 22 expose areas of seat 30.

Seat 12, FIG. 2, is a substantially circular, disc-shaped member having an upper planar surface 12a. First guide 14 has a first end 14a fixedly attached to planar surface 12a. A second end 14b of first guide 14 includes a threaded recess 39 for receiving a threaded end 41 of stabilizing member 20. Thus, stabilizing member 20 can be attached to and removed from first guide 14. A pair of lateral extensions 42a and 42b, FIG. 1, extend in opposite directions from first guide 14. Extensions 42a and 42b each include a threaded through-passage 44a and 44b, respectively. Although only one is fully shown, a threaded fastener 46 can be threaded into and through each passage 44a and 44b, and advanced to penetrate into insert 22 at seat 26.

An opening 48, FIG. 2, in first guide 14 receives second guide 16. A pin 50, attached to laterally extend from first guide 14, extends through an elongated, perpendicular slot 52 formed in second guide 16. As a result, second guide 16 is reciprocally movable relative to first guide 14, in directions indicated by the arrow designated R. A first end 16a of second guide 16 includes a threaded through-passage 54 for receiving a first threaded end 18a of extractor arm 18 which can be advanced through passage 54, permitting a tip 18b to be seated in one of the notches 36, and urged into contact with circular seat 30 of shell 24, see also FIG. 1. Handle 19, FIG. 1, at a second end 18c of extractor arm 18 facilitates advancing arm 18 into contact with shell 24.

A second end 16b FIG. 3, of second guide 16 includes a spring retainer 56 which is removably attached to second guide 16 by a fastener 58. Spring retainer 56 includes a stabilizing plunger 60 which seats within a metal compression spring 62, or the like. Spring 62 includes opposite ends 62a and 62b compressed between a seat 64 in spring retainer 56 and an opposed seat 66 in first guide 14. In this manner, second guide 16 is resiliently biased to move in lateral directions R relative to first guide 14.

In operation, seat 12 is seated in opening 27 of insert 22, and rotated until tip 18b of extractor arm 18 is resiliently urged to seat in a notch 36 by spring 62, and rest on circular seat 30 of shell 24. Stabilizing member 20 may be gripped to stabilize extractor 10, and at least one fastener 46 is advanced to penetrate insert 22 at seat 26. This secures extractor 10 to insert 22. Handle 19 of extractor arm 18 may be gripped to rotate and advance threaded end 18a of extractor 18, through threaded through-passage 54, thus forcing tip 18b against seat 30 of shell 24 in a direction indicated by the directional arrow designated D, FIG. 3. A reactive force eventually causes opposite movement of extractor 10 in a direction indicated by the directional arrow designated U, FIG. 3, which causes insert 22 to be snapped out of its engagement with shell 24.

As it can be seen, the principal advantages of these embodiments are that the plastic insert wear problem is substantially avoided by the addition of a metal inlay which lines the ball socket in the plastic insert. As a result, the flaking of plastic material is also avoided. In addition, the attachment of the first guide to the insert by a fastener permits extraction of the insert from the shell in response to the extractor arm being advanced in a direction opposite the direction of extraction. This avoids the need to pry or twist the shell attached to the acetabulum. Thus, the insert can be removed without causing damage to the shell.

As a result, one embodiment provides an acetabular insert extractor including a seat and a first guide attached to the seat for receiving a fastener. A second guide is movably attached to the first guide and an extractor arm is movably connected to the second guide.

Another embodiment provides an acetabular insert extractor for withdrawing an insert from a shell including a seat for engagement with the insert, and a first guide attachment to the seat for receiving at least one fastener for engagement with the insert. A second guide is movably mounted with the first guide, and an extractor arm is movably mounted with the second guide for engagement with the shell.

Still another embodiment provides an acetabular insert extractor system including a shell secured to a bone, and an insert snapped into engagement with the shell. A seat is provided for engagement with the insert, and a first guide is attached to the seat for receiving a fastener for securing the first guide with the insert. A second guide is movably mounted with the first guide, and an extractor arm is movably mounted with the second guide for forced engagement with the shell. As a result, the insert is snapped out of engagement with the shell.

A further embodiment provides an acetabular insert extractor for withdrawing an insert from a shell including a seat for seated engagement with the insert, and a first guide means attached to the seat for retaining a fastener in engagement with the insert. A second guide means connected to the first guide means for lateral movement relative thereto, and an extractor means is movably mounted in the second guide means for advancing into forced engagement with the shell. In this manner, the insert is urged out of engagement with the shell.

A still further embodiment provides a method of extracting an insert from an acetabular shell including the steps of positioning a seat on the insert and attaching the seat to a first guide. A fastener is inserted through the first guide and into the insert for securing the first guide to the insert. A second guide is mounted for lateral movement with the first guide, and an extractor member is mounted on the second guide. The second guide is moved relative to the first guide for positioning the extractor member adjacent the shell and for accommodating different size shells. The extractor member is advanced into engagement with the shell so that the fastener withdraws the insert from the shell.

Although illustrative embodiments have been shown and described, a wide range of modifications, change and substitution is contemplated in the foregoing disclosure and in some instances, some features of the embodiments may be employed without a corresponding use of other features. Accordingly, it is appropriate that appended claims be construed broadly and in a manner consistent with the scope of the embodiments disclosed herein.

What is claimed is:

1. An acetabular insert extractor for extracting an acetabular insert from an acetabular shell, comprising:
   a first guide having at least one through-passage;
   a threaded fastener engageable with the through-passage and adapted to penetrate the acetabular insert;
   a second guide movably connected to the first guide; and
   an extractor arm movably connected to the second guide.

2. The extractor as defined in claim 1 wherein the through-passage is threaded for threadably engaging with the fastener, and the threads on the fastener screw into the acetabular insert.

3. The extractor as defined in claim 1 wherein the second guide is movable laterally relative to the first guide.

4. The extractor as defined in claim 1 wherein the second guide is resiliently biased to move in a lateral direction relative to the first guide.

5. The extractor as defined in claim 1 wherein the extractor arm is threadably engaged with the second guide.

6. The extractor as defined in claim 5 wherein the extractor arm includes a handle attached to a terminal end thereof.

7. An acetabular insert extractor for withdrawing a polymeric insert from a shell, the acetabular insert extractor comprising:

a seat having a substantially circular configuration;

a first guide attached to the seat and having a bore;

an elongated fastener having external threads and being adapted to pass through the bore and penetrate into the polymeric insert;

a second guide movably mounted with the first guide; and an extractor arm movably mounted with the second guide for engagement with the shell.

8. The extractor as defined in claim 7 wherein the bore is threaded for engaging with the threads of the fastener, and the fastener is adapted to threadably screw into the polymeric insert.

9. The extractor as defined in claim 7 further comprising a second fastener having external threads; and wherein the first guide further includes a second bore for engaging the second fastener.

10. The extractor as defined in in claim 9 wherein both fasteners are adapted to threadably screw into the polymeric insert.

11. An acetabular insert extractor system comprising:

an acetabular shell;

an acetabular insert formed from a polymer and snapped into engagement with the shell; and an acetabular extractor adapted to extract the acetabular insert from the acetabular shell, the extractor including:
    a circular seat for engaging the acetabular insert;

a first guide attached to the seat;

a fastener engageable with the first guide and being adapted to penetrate into the acetabular insert;

a second guide movably mounted with the first guide; and an extractor arm movably mounted with the second guide for forced engagement with the shell, whereby the insert is snapped out of engagement with the shell.

12. The system as defined in claim 11 in which:

the acetabular extractor further includes a second fastener, wherein both fasteners have external threads; and the first guide has two separate through-passages, wherein each through passage threadably engages with one of the fasteners.

13. The system as defined in claim 12 wherein the insert includes a notch formed therein, and the second guide is biased to laterally urge one end of the extractor arm into the notch.

14. The system as defined in claim 13 wherein the extractor arm is threadably engaged with the second guide for advancing the one end of the extractor arm in a first direction into engagement with the shell, whereby the fastener and first guide are urged in a second direction, opposite the first direction, for withdrawing the insert from the shell.

15. An acetabular insert extractor for withdrawing an insert from a shell comprising:

a seat for seated engagement with the insert;

first guide means attached to the seat and having a through-passage;

a fastener removably engageable through the through-passage and adapted to screw into and penetrate the insert;

second guide means connected to the first guide means for lateral movement relative thereto; and extractor means movably mounted in the second guide means for advancing into forced engagement with the shell, whereby the insert is urged out of engagement with the shell.

16. The extractor as defined in claim 15 wherein fastener is threaded.

17. The extractor as defined in claim 15 wherein the insert includes a notch, and the second guide means is biased to urge one end of the extractor means into the notch.

18. The extractor as defined in claim 15 wherein the extractor means is advanced in a first direction into engagement with the shell and, in response, the insert is urged in a second direction, opposite the first direction.

19. A method of extracting an acetabular insert from a shell comprising the steps of:

positioning a seat on the insert, the seat being attached to a first guide;

mounting a second guide for lateral movement with the first guide;

mounting an extractor member on the second guide;

moving the second guide relative to the first guide for positioning the extractor member adjacent the shell;

inserting a fastener through the first guide and into the insert for securing the first guide to the insert; and advancing the extractor member into engagement with the shell so that the fastener withdraws the insert from the shell.

20. The method as defined in claim 19 wherein the step of mounting the second guide includes the step of resiliently biasing the second guide relative to the first guide.

21. The method as defined in claim 19 wherein the step of mounting the extractor member includes the step of threadably engaging the extractor member with the second guide.

22. The method as defined in claim 19 wherein the step of moving the second guide includes the step of resiliently urging the extractor member into a notch formed in the insert.

23. The method as define in claim 19 wherein the step of advancing the extractor member includes the step of advancing the extractor member in a first direction and in response, withdrawing the insert in a second direction, opposite the first direction.

* * * * *